United States Patent
Pak

Patent Number: 5,730,599
Date of Patent: Mar. 24, 1998

[54] PROTECTIVE DENTAL SHIELD

[76] Inventor: Elizabeth Y. Pak, 435 S. Detroit St. #202, Los Angeles, Calif. 90036

[21] Appl. No.: 745,440
[22] Filed: Nov. 12, 1996
[51] Int. Cl.$^6$ .................................................. A61C 5/14
[52] U.S. Cl. ........................ 433/215; 128/861; 433/140
[58] Field of Search ............................. 433/68, 69, 6, 433/215, 140; 128/861, 862, 859, 848

[56] References Cited

U.S. PATENT DOCUMENTS

| | | | |
|---|---|---|---|
| 648,028 | 4/1900 | Hooper | 128/848 |
| 2,192,558 | 3/1940 | Poindexter | 128/861 |
| 2,708,931 | 5/1955 | Freedland | 128/861 |
| 2,833,278 | 5/1958 | Ross . | |
| 3,307,539 | 3/1967 | Petersen | 128/861 |
| 4,044,762 | 8/1977 | Jacobs | 433/6 |
| 4,867,147 | 9/1989 | Davis . | |
| 4,944,947 | 7/1990 | Newman | 128/861 |
| 5,234,005 | 8/1993 | Kittelsen et al. | 128/861 |
| 5,462,066 | 10/1995 | Snyder | 128/862 |
| 5,469,865 | 11/1995 | Minneman . | |
| 5,562,106 | 10/1996 | Hreke et al. | 128/848 |
| 5,570,704 | 11/1996 | Buzzard et al. | 128/848 |

Primary Examiner—Paul J. Hirsch
Attorney, Agent, or Firm—Kelly Bauersfeld Lowry & Kelley, LLP.

[57] ABSTRACT

A protective dental shield made from a flexible and resilient material with a planar biting portion for placement between the occlusal surfaces of the upper and lower teeth of a patient and a pair of side walls projecting up and down from the spaced apart side edges of the biting portion to form a barrier between the side surfaces of the upper and lower teeth and the patient's soft tissue areas of the inner cheeks, tongue or lips. The protective dental shield is also provided with an extra-oral portion that extends beyond the patient's mouth when the shield is in place.

11 Claims, 2 Drawing Sheets

FIG. 1
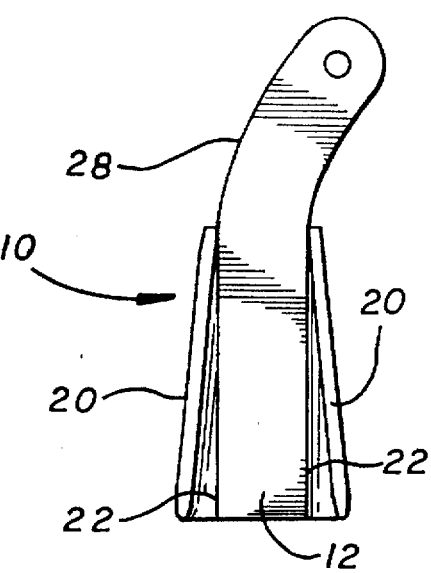
FIG. 3
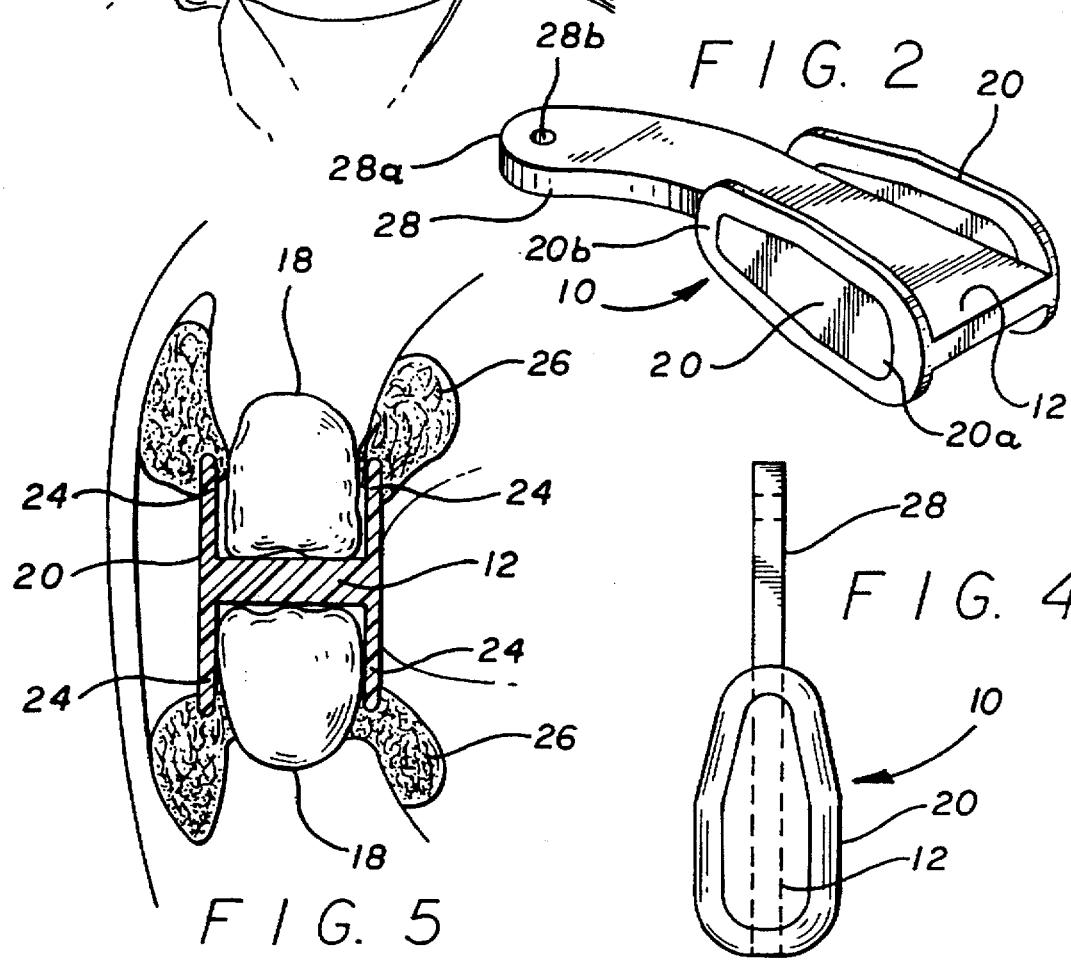
FIG. 2
FIG. 5
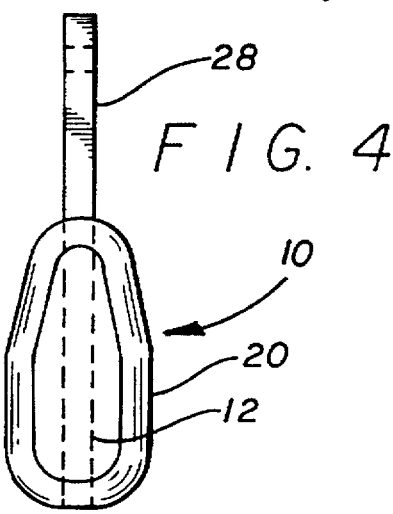
FIG. 4

PROTECTIVE DENTAL SHIELD

BACKGROUND OF THE INVENTION

This invention relates generally to devices used to protect against injuries to soft tissues such as cheeks, tongue and lips caused by accidental bites in anesthetized patients, and more particularly to a flexible dental shield for placement between the teeth so as to form a barrier around the teeth to isolate the teeth from the soft tissue areas.

Dentists, medical doctors and care providers often administer anesthetics (e.g., Novocaine) to cause a complete or partial loss of physical sensation, muscle function and pain before beginning oral treatments or surgery on their patients. Because areas of the lips, cheeks and tongue are often numbed and anesthetized along with the teeth, patients can, and often do, accidentally bite these otherwise sensitive soft tissue areas causing discomfort, bleeding, swelling and painful sores that may take several weeks to heal. In some cases, scarring of the bitten tissue may also occur. These problems are of great concern to patients and doctors, especially in cases involving the treatment of children who generally have a lower tolerance for pain than adults and also may be more prone to accidental biting of the numbed tissues.

In an attempt to prevent accidental bites and the resulting trauma in their patients, dentists or other medical practitioners often place a cotton roll or gauze padding inside the mouth on the side where the patient is numbed, and ask the patient to bite on the cotton or gauze and refrain from talking, chewing or engaging in other activities that may cause the patient to bite herself. The cotton roll or gauze padding is generally left inside the patient's mouth after the oral procedure until the numbness associated with the anesthetic wears off. While this method can provide some degree of prevention, it often provides an inadequate protection against accidental biting of soft tissue areas, and can be very uncomfortable for the patient.

Other oral devices have been designed and attempted in an effort to prevent accidental bite trauma and injury in patients. Some of these devices are not directed to patients with temporary numbness in the mouth area, and are of a more permanent nature such as those using arch wires in combination with hard oral acrylic devices designed for comatose patients or those with a long-term disability. Others utilize hard rubber or plastic mouth pieces, or flexible or inflexible bite splints over the occlusal surfaces of the teeth. In addition to their relative high cost and not lending themselves to be used readily and quickly without the need for special fitting, the non-flexible nature of such devices may cause damage to the surfaces of the teeth, soft tissues or filling material used to restore the teeth, and the wire or rigid plastic components may break away or cause the filling material to break away and be accidentally swallowed by the patient. Still other devices have been attempted which use flexible materials.

However, such devices have certain shortcomings in that some require the use of impressions or molds to fit the device for each patient, some require the wearer (typically an athlete) to place a device that covers the entire mouth area, and some only protect the occlusal surfaces of the teeth without providing a barrier around the side surfaces of the teeth, which increases the danger and possibility of accidental biting of soft tissue areas. Also, some of the existing designs are not particularly hygienic in that the portion of the device that is eventually placed inside the mouth must be touched or held prior to positioning it in the patient's mouth.

Thus, there is a need for a dental protective shield that can be manufactured inexpensively, is flexible and resilient so as to be comfortable, safe and adaptable to fit the maximum number of patients with a minimum number of sizes and shapes, provides a barrier around the occlusal and side surfaces of the upper and lower teeth so as to provide an effective protection against accidental biting of soft tissue surfaces, allows the wearer to breath and talk with minimal disturbance, enables the placement and removal of the device into and out of the patient's mouth in a hygienic and simple manner, and is disposable so as to eliminate cross-contamination problems. The present invention fulfills these needs.

SUMMARY OF THE INVENTION

The present invention resides in a dental protective shield made from a resilient and flexible material which forms a biting surface placed between the patient's upper and lower teeth with two side walls projecting from the two lateral side edges of the biting surface to form a barrier around the side surfaces of the patient's upper and lower teeth and an extra-oral portion.

More specifically, the dental protective shield of the present invention includes a biting portion formed from a planar piece of resilient material. Two side walls made from the same resilient material project from the two laterally spaced side edges of the biting portion above and below the planar surface of the biting segment. The outer extremities of the side walls are slightly angled or curved so as to provide space for the placement of the side walls against the gum tissue for a comfortable and secure fit. The biting segment and the side walls are shaped to follow the general contour and curvature of the teeth in the specific area of the mouth that has been anesthetized.

When the patient places the protective shield between the upper and lower teeth, the biting portion forms a barrier between the occlusal surfaces of the teeth, and the side walls form barriers between the side surfaces of the upper and lower teeth and the soft tissue areas of the patient's mouth such as the cheeks, lips and the tongue. In this manner, the protective shield of the invention essentially surrounds the occlusal and side surfaces of the upper and lower teeth to prevent accidental bites caused by contact between the teeth and the soft tissue areas.

In accordance with another aspect of the invention, an extra-oral portion is provided to allow the dental protective shield to be placed inside the patient's mouth in a hygienic fashion and to prevent accidental swallowing of the protective shield. The extra-oral portion is made from the same resilient material as the biting portion and the side walls. In the youth/adult version of the invention, the extra-oral portion extends from the biting portion, and is long enough to slightly protrude from the patient's mouth when the protective shield in place. Also, in the youth/adult version, the extra-oral portion may be provided with a hole to accept dental floss or other similar material therethrough so that in case the protective shield is accidentally swallowed by the patient, the dental floss can be used to retrieve and pull the protective shield from the patient's mouth. In the child version of the protective dental shield of the invention, the extra-oral portion extends from one of the side walls so as to take the form of a side flap outside the child's mouth to prevent accidental swallowing of the dental shield. The side flap can be flossed at the corner to further help prevent accidental swallowing of the dental shield.

Once the protective shield is placed inside the patient's mouth in the correct position and side, the patient bites on the biting portion and keeps the protective shield in his or her mouth until the numbness is gone or there is a need to temporarily remove the protective shield at which time the extra-oral portion is grasped to remove the shield from the patient's mouth.

The protective shield of the invention can be economically manufactured in a few sizes and shapes so as to follow the contour and size of typical molar and premolar teeth in most youths, adults and children. Since the shape and contour of the teeth on the left and rights sides of the mouth are symmetric, the protective shield of the invention can be easily flipped around and used for the molar and premolar teeth on both sides of the mouth.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is a perspective view of one embodiment of a protective dental shield made according to the present invention, wherein two such protective shields are shown in place on both sides of the mouth of the wearer.

FIG. 2 is an enlarged perspective view of the protective dental shield illustrated in FIG. 1.

FIG. 3 is a plan view of the protective dental shield illustrated in FIG. 2.

FIG. 4 is an elevational side view of the protective dental shield illustrated in FIG. 2.

FIG. 5 is an elevational cross-sectional view of the protective shield illustrated in FIGS. 1 and 2, taken generally along the line 5—5 of FIG. 1, showing the protective shield in contact with the wearer's teeth.

DETAILED DESCRIPTION OF THE PREFERRED EMBODIMENTS

Figure 6:
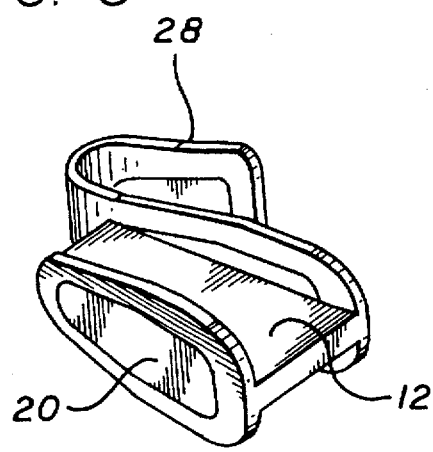
FIG. 6 is a perspective view of a second embodiment of a protective dental shield made according to the present invention.

As shown in the exemplary drawings, the protective dental shield of the present invention is illustrated generally at 10. The protective shield 10 is comprised of a generally elongated and planar biting portion 12 made of a resilient and flexible material such as plastic. The biting portion 12 has an appropriate size and shape so as to be capable of being easily placed in the mouth 14 of a patient 16 between a portion of the upper and lower teeth 18. The resiliency and flexibility of the material provides a safe and relatively soft surface for the patient to bite on, and allows the biting portion to maintain its shape even after being compressed under the pressure applied by the teeth. As illustrated in FIGS. 2 and 3, the biting portion 12 is trapezoidal in shape with its rear side being slightly wider than its front side to follow the natural contour of the set of teeth in the side of the mouth that are to be shielded.

A pair of side walls 20 also made of the same material as the biting portion project equal distances in upward and downward directions from the laterally spaced apart side edges 22 of the biting portion 12. As can be seen in FIG. 5, the side walls 20 are preferably substantially perpendicular to the biting portion 12, but other angles may also be used without interfering with the function of the side walls. Each side wall 20 includes a pair of legs 24 that extend away from the biting portion 12, which may engage adjacent gingival tissue 26. As illustrated in FIGS. 2 and 4, each side wall has somewhat of an oval shape positioned symmetrically with respect to the biting portion with the rear portion 20a of the side wall being wider than its tapered front portion 20b to provide a comfortable fit inside the mouth.

With this arrangement, when the patient 16 closes his or her upper and lower teeth 18 on the protective shield 10, the biting portion 12 and the side walls 20 form a barrier around the occlusal and side surfaces of the upper and lower teeth, and thereby prevent the accidental biting of the patient's cheeks, lips and tongue.

For purposes of illustration only and not by way of limitation, typically, in most youth/adult patients the width of the biting portion can be up to 0.5 inches on its front side, 0.75 inches on its back side, its length can be up to 1.5 inches, and can have a thickness of 0.05 to 0.15 inches. Similarly, the side wall used to fit most youth/adult patients can have a length up to 1.5 inches, and has a thickness of 0.05 to 0.1 inches. Also, the width of the side wall in its rear portion 20a can be up to 0.75 inches, and tapers down towards its front portion 20b with a width of up to 0.5 inches. For children, these dimensions can be reduced according to their age. To achieve economy in manufacturing the protective shield of the invention, it should be generally sufficient to offer the protective shield in two sizes to fit the vast majority of children, youths and adults. However, specific sizes and dimensions may be used to build protective shields to suit special needs of individual patients.

Furthermore, in accordance with the present invention, an extra-oral portion 28 is provided to enable the patient or other care provider to place the protective dental shield 10 inside the mouth of the patient while the numbness continues and to remove the shield after the numbness wears off or otherwise as needed. As illustrated in FIGS. 1-4, in one embodiment of the invention, the extra-oral portion 28 extends from the biting portion 12 so that when the protective shield is placed in the patient's mouth, the extra-oral portion protrudes a short distance from the mouth. The extra-oral portion 28 which is made of the same planar material as the biting portion is curved to follow the contour of the mouth with a rounded outer end 28a to provide safety. The extra-oral portion illustrated in FIGS. 2 and 3 is provided with a round hole 28b near its outer end 28a. The hole 28b is provided to allow dental floss or other similar means to be inserted and looped therethrough to enable the patient or care provider to grab the dental floss and pull the protective shield from the patient's mouth, should it be accidentally swallowed.

Figure 7:
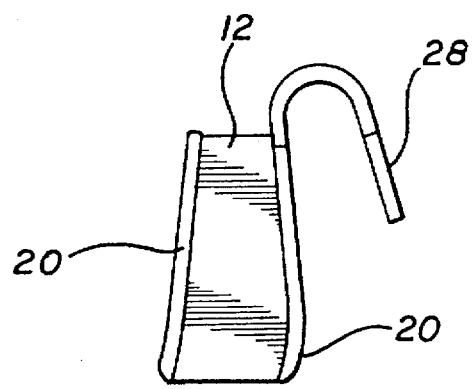
FIG. 7 is a plan view of the protective dental shield illustrated in FIG. 6.
Figure 8:
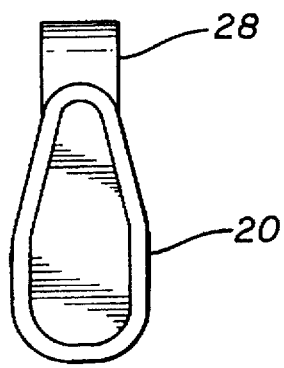
FIG. 8 is an elevational side view of the protective dental shield illustrated in FIG. 6.
Figure 9:
FIG. 9 is a perspective view of the protective dental shield illustrated in FIG. 6, shown in place in the mouth of the wearer.

In an alternative embodiment as illustrated in FIGS. 6-9, which is preferably used for children, the extra-oral portion 28 extends from one of the side walls 20 and curves away from the side wall so as to form a V-shaped side flap with the side wall. In this manner, the extra-oral portion 28 can remain against one side of the patient's cheek when the protective shield is placed inside the mouth and the corner of the side flap tied with floss, and cannot be accidentally swallowed.

In the embodiment of the invention illustrated in FIGS. 1-4, the extra-oral portion 28 is preferably integrally formed with the biting portion 12, but may alternatively be joined with the biting portion. Similarly, in the embodiment illustrated in FIGS. 6-9, the extra-oral portion is preferably integrally formed with one of the side walls 20, but may alternatively be joined with the side wall.

While the exemplary drawings illustrate a protective shield shaped for use in the sides of the patient's mouth, it is understood that the shape and measurements of the protective shield can be adjusted to fit the patient's front teeth should it be necessary to prevent accidental biting of soft tissue areas in the front area of the mouth. It is also understood that the specific shapes, sizes and thicknesses of the various portions of the protective shield of the invention can be modified and changed as long as it does not interfere with its effectiveness, safety and comfort to the patient.

From the foregoing, it will be appreciated that the present invention provides a means by which a flexible and resilient protective shield can be placed inside the mouth of the patient in the particular area of the mouth experiencing numbness or loss of control of the teeth to present a barrier between the patient's soft tissue areas of the cheeks, tongue and lips and the patient's occlusal and side surfaces of the teeth. Moreover, the present invention is provided with a flexible portion that extends beyond the patient's mouth to enable an easy, safe and hygienic placement and withdrawal of the protective shield into and out of the patient's mouth. The protective dental shield of the invention is also relatively easy and inexpensive to manufacture, and can be offered in several colors and standard (or special) sizes that can be used in any size or shape of teeth in all individuals.

While particular forms of the invention have been illustrated and described, it will be apparent that various modifications can be made without departing from the spirit and scope of the invention.

I claim:

1. A dental shield for protecting one side of a patient's mouth, comprising:

an elongated, resilient biting portion having first and second opposite planar sides and two laterally spaced apart side edges, said biting portion shaped for placement of said first and second opposite sides between occlusal surfaces of the patient's upper and lower teeth; and a pair of generally planar side walls made from a resilient material for forming barriers adjacent to both lateral sides of the patient's upper and lower teeth to isolate the teeth from the soft tissue areas of the patient's mouth, each side wall projecting from said laterally spaced side edges of the biting portion away from said first and second opposite sides of said biting portion.

2. The dental shield according to claim 1, further comprising an extra-oral portion extending from said biting portion outside the patients mouth.

3. The dental shield according to claim 1, further comprising an extra-oral portion extending from one of said side walls outside the patient's mouth.

4. The dental shield according to claim 3, wherein said extra-oral portion forms a V-shaped side flap with said one of said side walls, so as to be positioned exteriorly against one side of the patient's cheek when the biting portion is placed within the patient's mouth.

5. The dental shield according to claim 4, wherein said extra-oral portion includes an aperture adjacent to its end opposite said one of said side walls.

6. The dental shield according to claim 1, wherein said biting portion and said side walls are integrally formed.

7. The dental shield according to claim 1, wherein said biting portion and said side walls are homogeneously formed.

8. The dental shield according to claim 1, wherein said side walls are trapezoidally shaped.

9. A dental shield for protecting one side of a patient's mouth, comprising:

a biting portion made of an elongated planar piece of resilient material, said biting portion having first and second opposite sides with two laterally spaced apart side edges, said biting portion shaped for placement of said first and second opposite sides between occlusal surfaces of the patient's upper and lower teeth;

a pair of side walls made from a resilient material for forming barriers on both lateral sides of the patient's upper and lower teeth to isolate the teeth from the soft tissue areas of the patient's mouth, each side wall projecting from said laterally spaced side edges of the biting portion towards said first and second opposite sides of said biting portion; and an extra-oral portion extending from one of said side walls, wherein said extra-oral portion forms a V-shaped side flap with said one of said side walls, so as to be positioned exteriorly against one side of the patient's cheek when the biting portion is placed within the patient's mouth.

10. The dental shield according to claim 9, wherein said extra-oral portion includes an aperture adjacent to its end opposite said one of said side walls.

11. A dental shield for protecting one side of a patient's mouth, comprising:

a biting portion made of an elongated planar piece of resilient material, said biting portion having first and second opposite sides with two laterally spaced apart side edges, said biting portion shaped for placement of said first and second opposite sides between occlusal surfaces of the patient's upper and lower teeth;

a pair of side walls made from a resilient material for forming barriers on both lateral sides of the patient's upper and lower teeth to isolate the teeth from the soft tissue areas of the patient's mouth, each side wall projecting from said laterally spaced side edges of the biting portion towards said first and second opposite sides of said biting portion; and an extra-oral portion extending from said biting portion.

* * * * *